United States Patent [19]
Viner

[11] Patent Number: 5,902,816
[45] Date of Patent: May 11, 1999

[54] METHOD FOR TREATMENT OF HEAVY METAL POISONING

[75] Inventor: Norman M. Viner, Ottawa, Canada

[73] Assignee: Synapse Pharmaceuticals International, Inc., Ottawa, Canada

[21] Appl. No.: 08/803,721

[22] Filed: Feb. 21, 1997

[51] Int. Cl.$^6$ .......................... A61K 31/44; A61K 31/15
[52] U.S. Cl. ............................................ 514/334; 514/640
[58] Field of Search ....................................... 514/334, 640

[56] References Cited

U.S. PATENT DOCUMENTS

| | | |
|---|---|---|
| 2,816,113 | 12/1957 | Wilson et al. . |
| 2,847,308 | 8/1958 | Bersworth et al. . |
| 2,875,129 | 2/1959 | Bersworth et al. . |
| 2,947,782 | 8/1960 | de Benneville et al. . |
| 2,996,510 | 8/1961 | Green . |
| 3,063,901 | 11/1962 | O'Leary et al. . |
| 3,072,529 | 1/1963 | Sanders et al. . |
| 3,077,476 | 2/1963 | Hackley, Jr. et al. . |
| 3,852,294 | 12/1974 | Hagedorn . |
| 3,928,594 | 12/1975 | Cook . |
| 4,002,760 | 1/1977 | Cook . |
| 4,043,998 | 8/1977 | Meares et al. . |
| 4,352,810 | 10/1982 | Benschop et al. . |
| 4,675,326 | 6/1987 | Amitai et al. . |
| 4,865,837 | 9/1989 | Harris, III et al. . |
| 4,925,856 | 5/1990 | Harris, III et al. . |
| 4,988,710 | 1/1991 | Olney . |
| 5,206,371 | 4/1993 | Powers et al. . |
| 5,217,998 | 6/1993 | Hedlund et al. . |
| 5,443,847 | 8/1995 | West . |

FOREIGN PATENT DOCUMENTS 2016920  10/1979  United Kingdom .

*Primary Examiner*—Zohreh Fay
*Attorney, Agent, or Firm*—James W. Hellwege

[57] ABSTRACT

A method is provided for the treatment of heavy metal poisoning in a mammal comprising administering to a mammal including humans suffering from heavy metal poisoning a heavy metal chelating amount of an oxime.

12 Claims, No Drawings

METHOD FOR TREATMENT OF HEAVY METAL POISONING

BACKGROUND OF THE PRESENT INVENTION

The present invention is directed to a method for the treatment of heavy metal poisoning in a mammal.

Toxic contaminants such as heavy metals are widely present in the environment. Such contaminants come into contact with mammals such as humans on a regular basis. Such heavy metals include lead, cadmium, mercury, iron and the like. Exemplary sources of such metals includes contaminated water, contaminated wildlife (such as fish), plumbing, paints, auto emissions, and manufacturing processes. Recently, questions have even been raised regarding the safety of mercury amalgam fillings in teeth. Unfortunately, the presence of such contaminants in the body leads to a variety of health problems, including mental disfunction, coronary problems, circulation problems, nervous system disfunction, etc.

Exemplary heavy metal detoxification treatments are disclosed in U.S. Pat. Nos. 2,847,308 (calcium salt of calcium chelate); 2,875,129 (calcium chelate); 2,947,782 (aminoacetamidoximes); 3,072,529 (5-aminohexahydro pyrimidine); 4,043,998 (1-(p-benzenediazonium)-ethylenediamine tetraacetic acid); 5,217,998 (soluble polymer substrate having chelate attached thereto); and 5,443,847 (soluble manganese salt). Unfortunately, none of the above methods of treatment have been totally successful.

OBJECTS AND SUMMARY OF THE PRESENT INVENTION

It is accordingly an object of the present invention to provide a method for the treatment of or alleviation of symptoms of heavy metal contamination.

In accordance with the present invention, there is accordingly provided a method for the treatment of heavy metal contamination in a mammal comprising administering to a mammal including humans suffering from heavy metal contamination a therapeutically effective amount of an oxime chelating agent.

DETAILED DESCRIPTION OF THE PRESENT INVENTION

The present invention is directed to a method for treatment of heavy metal contamination in mammals.

The present invention involves the administration to a mammal suffering from heavy metal contamination a therapeutically effective amount of an oxime active agent, and preferably an oxime selected from the group consisting of bisquaternary and triquaternary oximes.

The oximes which may be employed in the present invention are well known to those skilled in the art and well-described in the literature. Such oximes found early use as nerve gas and toxic pesticide poisoning antidotes. Exemplary oximes include but are not limited to those compounds disclosed in U.S. Pat. Nos. 2,816,113; 2,996,510; 3,063,901; 3,077,476; 3,852,294; 3,928,594; 4,002,760; 4,352,810; 4,675,326; 4,865,837; 4,925,856; 4,988,710; 5,206,371 and U.K. application 2,016,920, each herein incorporated by reference in their entirety.

The oxime compounds which are be used in the present invention are defined by the formula $(R^1-CR=NOH)^+X^-$ where R is hydrogen, $C_{1-5}$ alkyl or $NH_2$ and $X^-$ is a pharmaceutically acceptable anion derived from a salt of an inorganic or organic acid. $R^1$ may take many forms. For example $R^1$ may be $C_{1-5}$ alkyl, aryl (e.g., phenyl), or a 5 or 6-membered heterocyclic moiety having from 1 to 3 nitrogen atoms in the heterocyclic ring.

The oxime may also be bicyclic in nature, as defined by the formula $R^1CR=NOH$ $X^-$ where R is hydrogen, $C_{1-5}$ alkyl or $NH_2$ and $R^1$ is

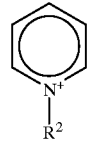

wherein $R^2$ is selected from the group consisting of:

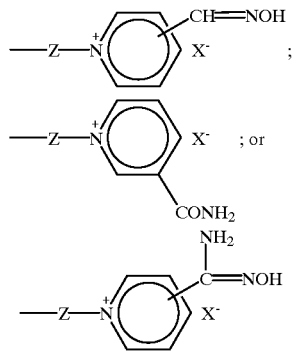

where Z is, for example, a polyalkylene group having from 1 to 6 carbon atoms, optionally including at least one ether linkage, such as $-CH_2CH_2-$, $-CH_2OCH_2-$, $-CH_2CH_2OCH_2CH_2-$, $-CH_2OCH_2CH_2OCH_2-$; or -$(CH_2)n$-phenyl-$(CH_2)n$- where n ranges from 1 to 6 and the phenyl moiety may be substituted by $C_{1-5}$ alkyl, and wherein $X^-$ is a pharmaceutically acceptable anion derived from a salt of an inorganic or organic acid.

Exemplary oxime chelating agents include the following oximes: 2-pyridine aldoxime methiodide, 4-pyridine aldoxime methiodide, methyl-2-pyridyl ketoxime methiodide, 1-methyl-pyridinium-2-aldoxime (2-PAM); 2,3-butanedione-2-oxime (DAM), pyruvaldehyde aldoxime (MINA), 2-pyridine aldoxime methochloride (2-PAM-Cl) (marketed as Protopam chloride), pralidoxime methylsulphate (marketed as Contrathion), obidoxime chloride (marketed as Toxogonin), 1,1'-polymethylene bis (4-formylpyridinium) halide oximes; 1,1'-(2,5-dimethyl-p-phenylenedimethylene) bis (4-formylpyridinium) halide dioximes; 1,1'-polymethylene bis (3-formylpyridinium) halide dioximes; 1,1'-(p-phenylenedimethylene) bis (3-formylpyridinium) halide dioximes; bis quaternary 4-formylpyriinium halide monooximes; 1,1'trimethylene bis (3-amidooximopyridinium) halides, quaternary pyridine aldoxime (TMB-4); HI-6; diacetyl monoxime; aldoxime-substituted triazolium compounds including 1,4-dimethyl-3-(hydroxyimino)methyl-1,2,4-triazolium chloride, 1-benzyl-3-(hydroxyimino)methyl-4-methyl-1,2,4-triazolium chloride, and 3-(hydroxyimino)methyl-1-methyl-4-(2'-methylsulfonyl-1'-ethyl)-1,2,4-triazolium chloride; and aldoxime-substituted imidazolium derivatives such as 1-([1'-(2'-butynyloxy)methyl]-2-(hydroxyimino)methyl-3-methylimidazolium chloride, 2-(hydroxyimino)methyl-3-methyl-1-[1'-2'-(methylsulfonyl)ethyloxy)methyl)-imidazolium chloride, 2-(hydroxyimino)methyl-3-methyl-1-[(2'-methyl-2'-nitropropyloxy)methyl]-imidazolium chloride, 1-[(2'-N,N-dimethylaminium)-1'-ethyl]2-(hydroxyimino)methyl-3- methylimidazolium chloride, 1-[2'-(hydroxyimino)methyl-3'-methyl-1'-imidazolo]-3-(4"-carbamoyl-1"-pyridino)propane dichloride, 1-(3'-bromopropyl-1'-oxy)methyl-2-(hydroxyimino)methyl-3-methylimidazolium chloride, 2-(hydroxyimino)methyl-3-methyl-1-(2'-pyrrdidinium-1'-)ethylimidazolium chloride hydrochloride, 1-(3'-butynyl-1'-thio)methyl-2-(hydroxyimino)methyl-3-methylimidazolium chloride, and 1-[(2'-N-ethyl-N-trifluoromethane sulfonyl) amino-1'-]ethyl-2-hydroxyimino)methyl-3-methylimidazolium chloride.

A preferred class of oximes suitable for use in the present invention may be depicted by the formula:

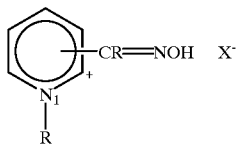

wherein R is hydrogen, $C_{1-5}$ alkyl, or $NH_2$; $R^1$ is $C_{1-5}$ alkyl (particularly methyl or ethyl), and X is an anion portion of the salt $R^1X$. Suitable acid addition salts include the chloride salt, the iodide salt and the methanesulfonate salt.

A specific oxime which is preferred for use in the present invention is 2-PAM chloride which is depicted by the following formula:

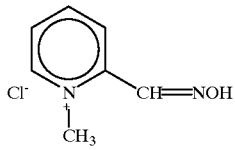

It is also advantageous to administer prodrug derivatives of oximes as disclosed in U.S. Pat. Nos. 3,929,813 and 3,962,447. Such prodrug derivatives exhibit an enhanced ability to pass the blood/brain barrier.

Oximes (such as 2-PAM and HI-6) have been used to provide in vivo protection against nerve gas agents and other organophosphate poisons. See, for example, U.S. Pat. Nos. 3,063,901; 4,713,391; 4,865,837; and 4,925,856. Also, one class of oximes (aminoacetamidoximes) is stated in U.S. Pat. No. 2,947,782 to be an effective sequestering agent for iron. However, the oximes of the present invention have not previously been employed to treat heavy metal toxicity in mammals such as humans. The amounts of the respective components required to provide the benefits of the present invention are orders of magnitude less than the amounts normally administered to provide protection against nerve gas agents or toxic organophosphate poisoning.

It is also within the scope of the present invention to combine administration of the oxime active ingredients with more conventional therapies such as antioxidant treatment, vitamin treatment, and other types of heavy metal antagonists. The identity of such compounds is well known to those skilled in the art as described in Goodman & Gilman's *The Pharmacological Basis of Therapeutics,* 9th edition, 1996.

It is within the scope of the present invention to employ both pharmaceutically acceptable analogs as well as tautomers, isomers and salts of the above listed compounds. Analogs differ from the above compounds by means of added alkyl or aryl substituents, added or deleted halogen moieties, presence of differing linkages such as ether linkage, saturation or unsaturation. As to possible salts, the present invention includes within its scope salts of alkali metals, alkaline earth metals, as well as acid addition salts of hydrochloric, hydrobromic, sulfuric, sulfamic, phosphoric, acetic, propionic, succinic, glycollic, stearic, lactic, malic, tartaric, citric, ascorbic, pamoic, maleic, hydroxymaleic, phenylacetic, glutamic, benzoic, salicylic, sulfanilic, fumaric, etc.

The compounds of the present invention may be administered by any pharmaceutically acceptable means and in any pharmaceutically acceptable form. For instance, the compounds may be administered orally in the form of pills, tablets, solutions, syrups, lozenges, etc. in which the compound is the sole or co-ingredient as the active agent. The compounds may also be administered parenterally (e.g., intravenously, intramuscularly or subcutaneously) in association with a pharmaceutically acceptable carrier. Topical administration such as by transdermal patch is also acceptable. The active components may also be administered by inhalers or internasally.

Tablets or pills may contain the active ingredient(s) in admixture with conventional pharmaceutically acceptable excipients (i.e., inert diluents). Such tablets or pills may be uncoated or coated by conventional techniques to delay disintegration and absorption in the gastrointestinal tract. More specifically, such tablets or pills may include an enteric coating to ensure disintegration and absorption in the intestine. Such coatings are generally comprised of a cellulose lower fatty acid phthalate such as cellulose acetate phthalate.

The oxime chelating agent is employed or administered in an amount effective to inhibit or decrease heavy metal toxicity. With the above in mind, the various compounds of the present invention may be administered within a wide range of dosage levels while still enabling the benefits of the present invention to be achieved. For example, the oxime chelating agent is generally administered at a dosage level of from about 1 mg to 10 mg. Such dosage levels are based on a standard adult body weight of 70 kg. Such dosage administrations are repeated as required to provide the desired results, with administrations being repeated every 12 to 36 hours depending upon the extent of heavy metal poisoning observed.

From the above description, one of ordinary skill in the art can readily ascertain the essential characteristics of the present invention. Without departing from the scope of the invention, various changes and/or modifications can be made which are still within the scope and range of equivalence of the attached claims.

What is claimed is:

1. A method is provided for the treatment of heavy metal poisoning in a mammal comprising administering to a mammal suffering from heavy metal poisoning a therapeutically effective amount of an active agent selected from the group consisting of:

(a) a compound defined by the formula $(R^1—CR=NOH)^+ X^-$ where R is hydrogen, $C_{1-5}$ alkyl or $NH_2$, $R^1$ is $C_{1-5}$ alkyl and $X^-$ is a pharmaceutically acceptable anion derived from a salt of an inorganic acid or a salt of an organic acid;

(b) a compound defined by the formula $(R^1—CR=NOH)^+ X^-$ where R is hydrogen, $C_{1-5}$ alkyl or $NH_2$, $R^1$ is aryl and $X^-$ is a pharmaceutically acceptable anion derived from a salt of an inorganic acid or a salt of an organic acid;

(c) a compound defined by the formula $(R^1—CR=NOH)^+ X^-$ where R is hydrogen, $C_{1-5}$ alkyl or $NH_2$ and $R^1$ is a 5 or 6 membered heterocyclic moiety having from 1 to 3 nitrogen atoms in the heterocyclic ring and X⁻ is a pharmaceutically acceptable anion derived from a salt of an inorganic acid or a salt of an organic acid;

(d) a compound defined by the formula (R¹CR═NOH X⁻ where R is hydrogen, $C_{1-5}$ alkyl or $NH_2$ and R¹ is

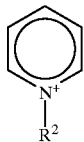

wherein R² is selected from the group consisting of:

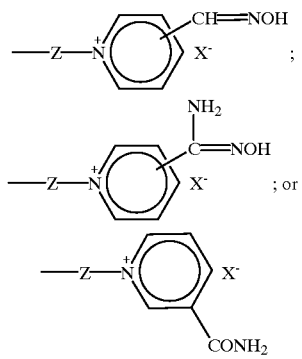

where Z is a polyalkylene group having from 1 to 6 carbon atoms, optionally including at least one ether linkage, or -($CH_2$)n-phenyl-($CH_2$)n- where n ranges from 1 to 6 and the phenyl moiety may be optionally substituted by $C_{1-5}$ alkyl, and wherein X⁻ is a pharmaceutically acceptable anion derived from a salt of an inorganic acid or a salt of an organic acid;

(e) a pharmaceutically acceptable prodrug derviative of a compound defined in (a), (b), (c) and (d) above; and (f) mixtures thereof.

2. The method of claim 1 wherein said active agent is selected from the group consisting of monoquaternary oximes, bisquaternary oximes, and triquaternary oximes.

3. The method of claim 1 wherein said active agent is an oxime salt.

4. The method of claim 3 wherein said salt is an acid addition salt selected from the group consisting of a chloride, iodide and methanesulfonate salt.

5. The method of claim 3 wherein said active agent is a chloride salt of an oxime.

6. The method of claim 5 wherein said active agent is 2-pyridine aldoxime methochloride (2-PAM Cl).

7. The method of claim 1 wherein said active agent is selected from the group consisting of 1-methyl-pyridinium-2-aldoxime (2-PAM), 2,3-butanedione-2-oxime (DAM), pyruvaldehyde aldoxime (MINA), bis quaternary pyridine aldoxime (TMD-4), pharmaceutically acceptable prodrug derivatives thereof and phamaceutically acceptable salts thereof.

8. The method of claim 1 wherein said mammal is a human and said active agent is administered in an amount within the range of from about 1 to 10 mg per 70 kg body weight.

9. The method of claim 1 wherein said active agent is defined by the formula (R¹—CR═NOH)⁺ X⁻ where R is hydrogen, $C_{1-5}$ alkyl or $NH_2$, R¹ is $C_{1-5}$ alkyl and X⁻ is a pharmaceutically acceptable anion derived from a salt of an inorganic acid or a salt of an organic acid.

10. The method of claim 1 wherein said active agent is defined by the formula (R¹—CR═NOH)⁺ X⁻ where R is hydrogen, $C_{1-5}$ alkyl or $NH_2$, R¹ is aryl and X⁻ is a pharmaceutically acceptable anion derived from a salt of an inorganic acid or a salt of an organic acid.

11. The method of claim 1 wherein said active agent is defined by the formula (R¹—CR═NOH)⁺ X⁻ where R is hydrogen, $C_{1-5}$ alkyl or $NH_2$ and R¹ is a 5 or 6 membered heterocyclic moiety having from 1 to 3 nitrogen atoms in the heterocyclic ring and X⁻ is a pharmaceutically acceptable anion derived from a salt of an inorganic acid or a salt of an organic acid.

12. The method of claim 1 wherein said active agent is defined by the formula R¹CR═NOH X⁻ where R is hydrogen, $C_{1-5}$ alkyl or $NH_2$ and R¹ is

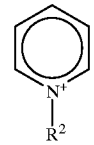

wherein R² is selected from the group consisting of:

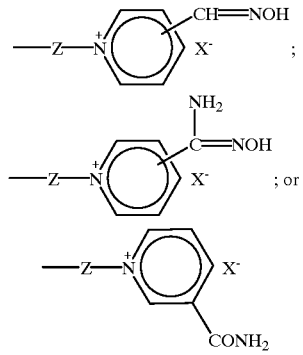

where Z is a polyalkylene group having from 1 to 6 carbon atoms, optionally including at least one ether linkage, or -($CH_2$)n-phenyl-($CH_2$)n- where n ranges from 1 to 6 and the phenyl moiety may be optionally substituted by $C_{1-5}$ alkyl, and wherein X⁻is a pharmaceutically acceptable anion derived from a salt of an inorganic acid or a salt of an organic acid.

* * * * *